United States Patent [19]
Bellis

[11] Patent Number: 5,278,256
[45] Date of Patent: Jan. 11, 1994

[54] RAPIDLY DEGRADABLE POLY (HYDROXYACID) COMPOSITIONS

[75] Inventor: Harold E. Bellis, Wilmington, Del.

[73] Assignee: E. I. Du Pont de Nemours and Company, Wilmington, Del.

[21] Appl. No.: 945,853

[22] Filed: Sep. 16, 1992

[51] Int. Cl.$^5$ .................. C08J 11/16; C07C 59/08
[52] U.S. Cl. .................. 525/450; 524/236; 524/428; 528/354; 528/361; 549/274; 562/579; 562/580; 562/584; 562/585; 562/589
[58] Field of Search .............. 524/236, 913, 910, 428; 523/124, 126; 528/354, 361; 525/450; 549/274; 562/579, 580, 584, 585, 589

[56] References Cited

U.S. PATENT DOCUMENTS

| | | | |
|---|---|---|---|
| 2,539,472 | 1/1951 | Ratchford et al. | 562/580 |
| 2,993,234 | 7/1961 | Miura et al. | 524/230 |
| 3,284,417 | 11/1966 | Hostettler et al. | 528/357 |
| 3,578,700 | 5/1971 | Klootwijk et al. | 560/185 |
| 3,654,212 | 4/1972 | Wright | 524/198 |
| 3,844,987 | 10/1974 | Clendenning et al. | 528/354 |
| 3,984,439 | 10/1976 | Vanlautem et al. | 562/579 |
| 4,444,881 | 4/1984 | Urbas | 562/589 |
| 4,727,163 | 2/1988 | Bellis | 549/274 |
| 4,797,468 | 1/1989 | De Vries | 528/354 |
| 4,835,293 | 5/1989 | Bhatia | 549/274 |
| 4,841,016 | 6/1989 | Edwards | 528/354 |
| 5,100,943 | 3/1992 | Katoh et al. | 524/230 |
| 5,110,868 | 5/1992 | Bellis et al. | 252/174.22 |
| 5,136,057 | 8/1992 | Bhatia | 549/274 |

FOREIGN PATENT DOCUMENTS

WO90/01521  2/1990  PCT Int'l Appl. .

OTHER PUBLICATIONS

*Kirk-Othmer Encyclopedia of Chemical Technology*, 3rd Ed., vol. 19, pp. 521–531 (1984).
*Ullmann's Encyclopedia of Industrial Chemistry*, vol. A19, pp. 293–298 (1987).

*Primary Examiner*—Veronica P. Hoke

[57] ABSTRACT

The depolymerization of poly(hydroxyacids) in a liquid medium is enhanced by the presence of a quaternary ammonium compound. Poly(hydroxyacid) polymers containing a quaternary ammonium salt are more readily depolymerized.

20 Claims, No Drawings

RAPIDLY DEGRADABLE POLY (HYDROXYACID) COMPOSITIONS

BACKGROUND OF THE INVENTION

1. Field of the Invention

This invention relates to poly(hydroxyacid) compositions and articles manufactured therefrom which have increased rates of polymer depolymerization relative to the conventional polymeric compositions and articles. An aspect of this invention relates to methods for making such compositions. Another aspect of this invention relates to a method for recovering hydroxyacid monomer from the depolymerized poly(hydroxyacid). Still another aspect of this invention relates to a medium, containing the poly(hydroxyacid) composition, from which the monomer can be recovered.

2. Description of Related Art

Poly(hydroxyacids) ("PHA's") such as polyactic acid ("PLA") and polyglycolic acid ("PGA") have been known for many years. Among the important properties of these polymers are their tendency to depolymerize relatively easily and their ability to form environmentally benign byproducts when degraded or depolymerized. Consequently, high molecular weight PHA polymer shaped articles are finding increasing application as replacements for non-degradable polymers such as polystyrene in throw-away products like fast-food containers (Sinclair et al, WO90/01521, published Feb. 22, 1990).

Hydroxy(carboxylic acids) such as lactic acid or their cyclic diesters (in the case of lactic acid the cyclic diester is called "lactide"; in the case of glycolic acid it is called "glycolide") can be polymerized to a PHA such as PLA or PGA. See U.S. Pat. No. 4,797,468 (De Vries), issued Jan. 10, 1989, and also U.S. Pat. No. 4,835,293 (Bhatia), issued May 30, 1989, and U.S. Pat. No. 4,727,163 (Bellis), issued Feb. 23, 1988.

The ease of depolymerization of the poly(hydroxyacids) is generally attributed to ester linkages which are hydrolyzable under mild conditions and/or to greater hydrophilicity as compared to most polyesters. By contrast, typical commercially-used polyesters derived from aromatic dicarboxylic acids and glycols are far less hydrophilic, and their ester linkages are, for all practical purposes, hydrolysis resistant under the type of conditions encountered in a landfill and even under more severe conditions.

The environmentally benign character of the degradation products of PHA's has potential for simplifying or even reducing litter and other waste disposal problems, e.g. in the management of long-term landfills.

While increased use of PHA's can theoretically have a favorable impact on environmental problems, simply discarding high molecular weight PHA articles for destruction by hydrolytic degradation has the cost penalty of discarding the valuable, potentially recoverable hydroxyacid (HA) moieties.

In manufacturing operations in which high molecular weight polymers are shaped to form stock material and particularly to form useful articles, re-use or recycling of factory waste (mold flash, trim waste, etc.) is desirable but not always practical. Theoretically, an ideal way to use polymeric factory waste would be to depolymerize it and recover the monomer or monomers from which it was made.

Although it is clearly impractical (if not impossible) to carry out on-site depolymerization of factory waste made up of only hydrolysis-resistant conventional polyesters, the development of new uses of PHA's suggests a faster route to recovery of valuable monomers from the PHA factory waste, perhaps through the use of an on-site hydrolytic medium, provided the rate of hydrolysis would be rapid enough. Hydrolysis of PHA's is in fact well known, but rates of hydrolysis presently appear to be too slow for treatment of factory waste and the like. In PHA hydrolysis, PHA polymer (including articles formed from PHA) is collected and is typically exposed to water for a long period of time. The end product of the hydrolysis is a low molecular weight oligomer and/or a fundamental acid moiety such as lactic acid (the end product obtained from hydrolysis of PLA) or glycolic (hydroxyacetic) acid (the end product obtained from hydrolysis of PGA). In short, depolymerization of PHA's via the hydrolytic route, though promising, can be very slow.

It has therefore not been possible to achieve depolymerization of PHA's within a time frame which would permit practical recovery and reuse of valuable HA moieties. And even in the case of landfills, the time required for degradation of high molecular weight PHA's is too long to provide a noticeable lessening of the burden on the landfills.

U.S. Pat. No. 5,136,057 (Bhatia), issued Aug. 4, 1992 discloses a process for recovering recyclable lactic acid from impure lactide, and U.S. Pat. No. 5,110,868 (Bellis), issued May 4, 1992 discloses a water-degradable molded object containing low molecular weight ($MW \leq 4000$) poly(lactic acid/glycolic acid), a nonionic surfactant, and a large content of a water soluble inert salt. Sinclair et al, WO90/01521, utilize entrapped lactic acid or lactic acid oligomers to speed up degradation of high-MW PHA's, but more typically the art does not address the problem of providing rapid depolymerization of high-MW PHA (e.g. polymeric articles made from PHA). Nor does the art appear to address adequately the problems of providing practical routes to the recovery of fundamental moieties (e.g. HA's) from high molecular weight PHA's (e.g. from high molecular weight PHA factory waste or from used disposable articles formed from PHA).

SUMMARY OF THE INVENTION

It has now been discovered that the depolymerization rate of PHA's, including high molecular weight ($MW > 2500$, preferably $> 5000$) poly(hydroxycarboxylic acids) can be enhanced significantly by introducing an ammonium compound, preferably a quaternary ammonium compound (a "quat") into the PHA. Useful monomeric compounds such as HA's can be recovered from the depolymerization medium. The benefits of this invention are effectively obtained when the quat (depolymerization enhancer) is substantially fully distributed throughout the PHA mass, but, surprisingly, contacting a quat-free PHA mass with a depolymerization medium containing the quat appears to have little or no effect upon the rate of depolymerization. It is preferred that a surfactant also be distributed throughout the PHA. Quat-containing PHA's and quat-containing PHA articles of this invention can be prepared, for example, by introducing powdered quat into molten, high molecular weight PHA or by introducing powdered quat during the synthesis of the high molecular weight PHA from a low molecular weight starting material.

DEFINITIONS

The term "substantially fully distributed", as used this specification in connection with a molten or solid polymeric material (such as a mass of pHA) means dissolved, suspended, or dispersed in the polymeric material. In the case of a solid polymeric material, a "substantially fully distributed" quaternary ammonium compound is in a state of solid solution or is a particulate solid phase suspended or dispersed in a solid matrix of polymeric material. Completely uniform distributions (e.g. true solid solutions) of quaternary ammonium compounds ("quats") in typical poly(hydroxycarboxylic acids) may be difficult to attain, but are not absolutely necessary. A high degree of intimate admixture and distribution, e.g. dispersion or suspension can be obtained by, for example, introducing powdered quat into a molten mass of polymer. (The terms "suspension" and "dispersion" normally denote very similar phase relationships, except that "suspended" particles or "suspensoids" are generally larger than "dispersed" particles or "dispersoids"; dispersoids can be as small as colloidal in size and can provide distributions of particles throughout a matrix or mass with a significant degree of uniformity.) The term "substantially" is included in this term in order to indicate that some degree of nonuniformity of distribution is permitted and can even be useful, as in the case of a concentration of quat at or near the surface of an article, so that depolymerization is initially accelerated by the higher concentration of depolymerization enhancing agent in the region where PHA is in contact with liquid depolymerization medium.

The term "polymer" as used in this specification refers to homopolymers and copolymers (including terpolymers and polymers of four or more different monomers and mixtures of such polymers). A "polymeric" substance or article is a substance or article which comprises a "polymer" as defined herein. The "polymers" contemplated for use in this invention are room-temperature solids having a multiplicity of repeating units or moieties and hence are of higher molecular weight than dimers, trimers, etc. and, generally speaking, are of higher molecular weight than oligomers.

DETAILED DESCRIPTION

It has been found that the rate of hydrolysis depolymerization of PHA's is significantly increased if a quaternary ammonium compound (quat) is substantially fully distributed throughout the PHA as a depolymerization enhancing agent. This permits the use of lower depolymerization temperatures and/or increases the speed of hydrolysis.

Products which embody the principles of the present invention therefore comprise PHA with depolymerization enhancer (quat) substantially fully distributed therethrough. A surfactant can optionally be included in the product. Fillers, pigments, stabilizers, and similar ingredients typically included in molding compositions are also optionally added. These PHA products can be in the form of molding compositions (including moldable masses of pellets or granules or the like) or bulk form or in the form of articles or stock items which have been shaped by spinning, extrusion, molding, melt-casting, etc.; fibers or filaments, films, foams, molded articles such as food containers and the like being typical of shaped material or articles which can be made from PHA's. After use, depolymerization-enhanced PHA articles of this invention can be discarded in waste landfills, where they are quickly hydrolyzed to environmentally benign low molecular weight products, such as a hydroxycarboxylic acid monomer that poses no danger to groundwater and is rapidly degraded to water and $CO_2$.

Substantially complete distribution of a quat throughout a PHA can be provided by, for example, adding the quat to molten high molecular weight PHA or introducing the quat during the synthesis of the high molecular weight PHA from low molecular weight precursors or monomers. In the melt-blending method, a fusible high molecular weight PHA is melted and the quat (which is normally in the form of a finely divided powder) is intimately mechanically blended into the molten PHA. For example, a Brabender blender, operated at a temperature selected so as to maintain a liquid or molten mass of relatively low viscosity, is well-suited to the blending step. The objective here is to incorporate the depolymerization enhancing agent or agents substantially uniformly throughout the PHA mass, so that when depolymerizing the PHA adequate depolymerization enhancer will always be present at the PHA surface which is in contact with the liquid depolymerization medium.

The melt-blending technique is particularly well suited to introducing other depolymerization enhancing ingredients or conventional additives such as fillers, pigments, stabilizers (e.g. sun blockers), and the like. Cationic, anionic, amphoteric, and nonionic surfactants—particularly nonionic surfactants—appear to assist the quat in providing depolymerization enhancement. Thus, a preferred aspect of this invention involves co-blending the quat with a surfactant. Again, the objective here is to incorporate depolymerization enhancers and other additives substantially completely throughout the PHA, so that other desired additives (particularly the surfactant) can also be present at the depolymerization medium/PHA/quat interface.

As is known in the detergent art, compounds with nonionic surfactant properties are typically obtained by synthesizing a molecule with the desired hydrophobe-/hydrophile balance. The hydrophobicity of the surfactant can be attributed to long-chain aliphatic or alkyl-aromatic residues or oxypropylene or oxybutylene units or chains, and the hydrophilicity can be attributed to oxyethylene units or chains (typically provided by reacting an alkyl-phenol or long-chain aliphatic alcohol with ethylene oxide or an ethylene oxide/propylene oxide mixture high in ethylene oxide). Thus, typical nonionic surfactants can be ethylene oxide/propylene and/or butylene oxide random or (more typically) block copolymers, a reaction product of a generally straight-chain $C_6$–$C_{24}$-alkyl-phenol with ethylene oxide, a reaction product of a generally straight-chain $C_6$–$C_{24}$-aliphatic alcohol with ethylene oxide, etc. Alkyl-phenols such as nonylphenol and alcohols such as 1-octanol, 1-decanol, laury alcohol, palmityl alcohol, stearyl alcohol, etc. are often used to make such nonionic surfactants.

As noted previously, some degree of nonuniformity of distribution of the quat can be useful, particularly when the quat tends to be concentrated near the surface of the PHA article or material.

Concentration of quat near the surface of the PHA can readily be provided when the second method of preparation of depolymerization-enhanced PHA is used. In this method, the quat, any optional depolymerization enhancing or assisting additive, and optional conventional additives can be added during the synthesis of PHA toward the end of the polymerization when little or no water is present. This method can be carried out batchwise, continuously, or semi-continuously, so long as the quat and the optional additives are thoroughly mixed throughout the final PHA. When added sufficiently near the end of the polymerization, the quat and the optional additives can be caused to concentrate near the surface of the PHA material or article.

PHA molding compositions of this invention, which comprise PHA, a quat substantially fully distributed therethrough, and, optionally, a surfactant and one or more conventional molding composition additives can then be thermoformed into final objects of use, such as by pressure or inflation molding. Similar compositions can be used in casting, extrusion, spinning, etc. Alternatively the PHA containing an appropriately high content of depolymerization enhancer can be pelletized as a pre-mix or masterbatch to be mixed, such as by ball milling or co-melting, with PHA not containing the enhancer.

The quaternary ammonium compound is preferably distributed (e.g. dispersed) as intimately as possible throughout the polymer so that during depolymerization in a depolymerization medium (such as a polar solvent) there is always present in intimate contact at the PHA surface three ingredients; namely, PHA, depolymerization medium, and quaternary ammonium compound. If the depolymerization medium is aqueous, rapid economical depolymerization of the PHA occurs, and the hydroxy acid (HA) moieties and PHA oligomer products can be recycled to PHA manufacture or can be discharged to the environment without damage.

This invention is useful with a wide range of PHA's. The PHA art has been under development for many years, hence the variety of PHA's known in the art is extensive.

The PHA's presently of greatest commercial interest are the poly(hydroxycarboxylic acids), which typically are polymers of the general formula —(—Y—CO—O—)$_m$—, where Y is a straight or branched aliphatic chain having 1 to 8 carbon atoms in the backbone of the chain and which can optionally be interrupted by one or more heteroatoms (e.g O, N, etc.), and n is the degree of polymerization. These polymers are obtained from the corresponding hydroxycarboxylic acids or their lactones or other cyclic esters. The hydroxycarboxylic acids themselves can (without being converted to the corresponding acid halides) eliminate H$_2$O in a condensation reaction and thereby form polymer chains with the characteristic recurring ester units shown in the above general formula, but the molecular weight of such condensation polymers tends to be low. Better (e.g. higher molecular weight) polymers are generally obtained when a cyclic ester such as a lactone or a cyclic diester (e.g. lactide and/or glycolide) is subjected to a ring-opening reaction. The cyclic diesters and lactones can react with each other or with other monomers or initiators or ring-opening agents. The preparation of cyclic diesters from various starting materials (e.g. by decomposition of a low molecular weight PHA) and the preparation of PHA's from these diesters are described in the patent literature, e.g. in U.S. Pat. Nos.

4,727,163 (Bellis), issued Feb. 23, 1988,
4,797,468 (De Vries), issued Jan. 10, 1989, and
4,835,293 (Bhatia), issued May 30, 1989.

Preparation of PHA's from lactones ("lactone polyesters") is disclosed in, for example, U.S. Pat. Nos.

3,284,417 (Hostettler et al), issued Nov. 8, 1966 and
3,578,700 (Klootwijk et al), issued May 11, 1971.

The cyclic diester starting materials referred to above can be obtained from an o-hydroxycarboxylic acid or low molecular weight oligomers or polymers of an α-hydroxycarboxylic acid of the formula HO—CR$^a$R$^b$—COOH where R$^a$ and R$^b$ are the same or different and are hydrogen or lower alkyl. The cyclic diester preferably has six ring members (the term "ring members", as used in this discussion, includes the carbonyl carbon and the oxy group linked to the carbonyl carbon), and these cyclic esters (e.g. lactide and glycolide), when sufficiently pure, can provide high quality poly(hydroxycarboxylic acids).

In addition to the cyclic esters, industrially practical hydroxyacid monomers can include open-(straight or branched)-chain hydroxycarboxylic acids in which the hydroxyl group is in the 2-, 3-, 4-, 5-, 6-, or omega-position and lactones having 4 to 9 (preferably 4 to 7) ring members, wherein the term "ring members" is used as indicated above. The straight or branched open chain of the hydroxycarboxylic acids is typically aliphatic, including aliphatic chains interrupted by hetero-atoms (preferably hetero-atoms such as O or N). Preferred lactone monomers have an aliphatic chain residue which also can be interrupted by hetero-atoms, particularly when the aliphatic chain residue occupies three or more ring positions. Moreover, the aliphatic chain residue can be substituted with, for example, open-chain aliphatic groups such as lower alkyl radicals.

Thus, the preferred "monomers" (the term "monomer" should be understood to include the dimeric cyclic esters) are compounds of formulas I, II, or III.

HO—A—COOH  (I)

 (II)

 (III)

where

A and A' are preferably straight or branched aliphatic chains which can contain one or more heteroatoms (e.g. O, N, etc.) in place of carbons in the aliphatic chain; typically, A contains from 1 to 8 carbon atoms in the backbone of the chain (which backbone can be substituted with lower aliphatic radicals or the like); A' is typically a straight or branched chain lower alkylene group such as —C(R$^1$)(R$^2$)—C(R$^3$)(R$^4$)—, where R$^1$ to R$^4$ are the same or different and are H or methyl;

Z is the aliphatic residue of a lactone, which residue can contain one or more hetero-atoms (O, N, etc.). Typically, Z contains 2 to 8 (preferably 2 to 6) ring members, all of which may be carbon atoms, but when the number of ring members in Z is at least 3, one of the ring members can be a heteroatom.

Monomers of formula I, II, or III which have different general formulas can be copolymerized (e.g a monomer of formula II with a monomer of formula III) and-/or reacted with a monomeric or low molecular weight polyfunctional alcohol, amine, or similar compound having ring-opening capabilities (which can serve as the "hub" of a "star" polymer or the branching point of a branched polymer), and two or more monomers within the scope of the same formula (e.g. two monomers of formula III) can be copolymerized with each other.

Particularly preferred monomers of formula I are α, β, or omega-hydroxycarboxylic acids, e.g. glycolic acid, lactic acid (both of which are α-hydroxyacids), β-hydroxypropionic acid, β-hydroxybutyric acid, and omega-hydroxycarboxylic acids such as δ-valorolactone, ε-caprolactone, etc. When the monomer of formula I (or the lactone or other cyclic ester thereof) contains a secondary or tertiary OH, the carbon atom to which it is attached is likely to be an asymmetric center and hence optically active. Lactic acid and β-hydroxybutyric acid are just two examples of hydoxycarboxylic acids which can have D- and L-forms and can form racemic mixtures. The DL-racemates, D-forms, mixtures of D-forms and DL-racemates, L-forms, and mixtures of DL-racemates and L-forms are all operative. In some cases, higher quality polymer products can be obtained with a starting material that is primarily (e.g. >80%) L-isomer. Commercial interest is normally focussed on poly(hydroxyacids) which are environmentally friendly and/or easily depolymerized.

Particularly preferred monomers of formula II are ε-caprolactone, δ-valerolactone, 1,4-dioxan-2-one, β-butyrolactone, β-propiolactone, 6-methyl-2,5-morpholinedione, 1,5-dioxepan-2-one, and mixtures thereof.

Of all these monomers, the ones of greatest commercial interest are presently lactic and/or glycolic acid (or lactide and/or glycolide), which are polymerized individually or in combination or, individually or in combination, are polymerized with up to 30 weight-% of a lactone comonomer.

The particular other monomer units present in the PHA to be depolymerized are not critical, the present process having wide applicability in depolymerizing and recovering the monomer values of PHA's.

While the invention has been described with particular reference to the depolymerization of PHA's, it has broad applicability to polyesters in general where the polyester composition is not completely hydrolysis-resistant and the quaternary ammonium compound is therefore able to assist in breakdown of ester linkages. Thus the invention has at least marginal utility in depolymerizing other polyesters such as those containing small amounts of polyethyleneterephthalate.

This invention is useful for virtually the entire range of PHA average molecular weights, from the oligomers of MW as low as several hundred to high polymer MWs of 1,000,000 or more. Techniques for exerting control over number average or weight average molecular weights are known in the art. The present invention is of greatest interest in connection with enhancing the depolymerization of polymers having number average or weight average molecular weights of at least about 2500, e.g. 5000 to 800,000. Of course, mixtures of oligomers and polymers can form during the polymerization reaction, but techniques have been developed to maximize polymer formation (e.g. by utilizing cyclic diester starting materials) and/or to remove oligomeric components from the polymerized product.

The PHA can be amorphous or crystalline, but the PHA's of greatest interest in relation to this invention (particularly in the case of PHA's of MW 2500 to 800,000) have a significant degree of crystallinity; that is, they are predominantly non-amorphous in nature.

Ammonium compounds useful in the process and products of the invention have the formula:

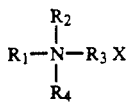

wherein $R_1$, $R_2$, $R_3$, and $R_4$ can be the same or different and are H or (preferably) organic groups, and X is an anion of an organic or mineral acid and can be present as one equivalent of a polyvalent anion such as sulfate, phosphate, etc.

Typically, $R_1$ through $R_4$ are cycloaliphatic (e.g. $C_5$- or $C_6$-ring cycloaliphatic), aromatic (preferably monocyclic aromatic), or $C_1$-$C_{36}$ aliphatic (including aryl-aliphatic, e.g. benzyl, and other substituted aliphatic radicals), or two or more of the groups $R_1$ through $R_4$ can, together with the N-atom, form a heterocyclic ring such as a pyridinium, imidazolinium, or morpholinium ring. $R_1$-$R_4$ are most preferably fully or substantially fully saturated $C_1$-$C_{24}$-aliphatic residues such as alkyl groups; at least one of the alkyls preferably has less than 4 carbon atoms, and typically as many as 3 or 4 of the alkyls can have 8 or fewer carbon atoms. Although ammonia and amines are easily protonated to form an N-cation having a tetravalent N-atom, it is ordinarily preferred that none of the N-substituents be protons, so that the $R_4N^+X^-$ salt will have optimum phase-transfer catalysis capabilities. From the standpoint of commercial availability of quaternary compounds, it is preferred that $R_1$ through $R_4$ be "alkyl" in the broad sense of substituted or unsubstituted alkyl, so that "alkyl" includes aryl-alkyl (e.g. benzyl), oxy-substituted alkyl (e.g. hydroxyalkyl, ether or polyether structures such as oxyethylene or polyoxyethylene, ethoxylated unsaturated residues, etc.), particularly 2-hydroxyethyl, as in choline halides, or other N- or O-containing alkyl derivatives, e.g. amido-substituted alkyl, etc.

X is preferably the anion of a relatively strong acid, because neutral quaternary ammonium salts can provide the greatest ease of distribution throughout the PHA. Thus, X can be, for example, halide, alkylsulfate (particularly methylsulfate), aryl- or alkyl-sulfonyl, phosphonyl, or one equivalent of sulfate or phosphate. Quats in which X is chloride, bromide, iodide, and/or $CH_3O-SO_2-O^-$ are particularly desirable because of the outstanding commercial availability of quaternary ammonium halides and methylsulfates. As indicated above, quats used in this invention can be selected for solubility or dispersibility in molten PHA, and these quats are also selected for minimal chemical reactivity with depolymerization media such as water and minimal reactivity with the polymer depolymerization products. Preferably the quat is also soluble in the depolymerization medium.

The preparation and commercial utility of quats is described in detail in the encyclopedia article entitled "Quaternary Ammonium Compounds", Kirk-Othmer, Encyclopedia of Chemical Technology, Vol. 19, p. 521 et seq., and a further discussion of one of the many uses of quats can be found in another encyclopedia article entitled "Phase Transfer Catalysis", Ullman, Encyclopedia of Industrial Chemistry, Vol. A19, p. 293 et seq, particularly on page 294.

Excellent quaternary ammonium salts include:
tetrabutylammonium bromide (TBAB)
benzyltrimethylammonium chloride
methyltricaprylammonium chloride ("Arosurf PT64")
methyltributylammonium chloride (MTBC)
triethylbenzylammonium chloride
octyltrimethylammonium bromide (OTMAB)
choline chloride The amount of quaternary compound used depends on the MW of the PHA, the extent and speed of desired depolymerization, and the nature of the PHA material or article (in the case of a masterbatch, the quat concentration is several times greater than that of a fiber, film, molded article, or the like). It also depends on the particular depolymerization medium, such as water, acid, alcohol, amide and the like; and the temperature, pressure and time of depolymerization. Higher temperature, pressure and longer time of depolymerization permit the use of lower quantities of a particular quaternary ammonium compound. For landfill disposal, where the liquid medium is at ambient temperature and pressure, from about 0.1 to 10% of quat based on the weight of the polymer is appropriate. The amount will be less under high temperature conditions than under low temperature conditions.

For a masterbatch, the amount of quat can range from about 1 to about 30 or 40% by weight of the PHA.

The mechanism by which the quaternary ammonium compound enhances PHA hydrolysis is not completely understood. Although this invention is not bound by any theory, it is presently believed that the overall effect of the quat is to expedite hydrolysis of the ester bond. The quat may play a chemical role in the hydrolysis, but after depolymerizing hydrolysis the quat remains as such dissolved in the hydroxyacid product solution. It is also theorized that typical PHA polymer chains assume a helical geometry, and the quat tends to associate with one end of the helix, a little like a weight at the end of a coiled spring. If this be correct, the surprising efficacy of the quat can perhaps be explained in terms of its strategic location at the end of the polymer chain, where chain depolymerization would be expected to commence. Quat characteristics of this type appear to make it possible for the substantially uniformly distributed quat to become more concentrated near the surface of the PHA, despite continuous stirring of the melt into which the quat is introduced.

The depolymerization medium is a liquid that at depolymerization temperature is reactive with (solvolytic toward) the PHA and non-reactive with the depolymerization products, and which can be a solvent for the depolymerization products and preferably also the quaternary ammonium compound. The common medium in a landfill is water, possibly contaminated with other landfill ingredients, and aqueous media are convenient to use under almost any circumstances. Aqueous depolymerization media can contain salts (including the same quaternary ammonium salts dissolved, dispersed, or suspended in the PHA), acids, bases, etc. Other suitable depolymerization media include ammonia ($NH_3$) and polar organic liquids with solvent and/or solvolytic properties which contain an oxy (e.g. OH or ether), amino, carbonyl, acid (carboxyl, etc.) or other polar group, protic solvents such as lower aliphatic alcohols, organic and mineral acids, and lower aliphatic (including OH-substituted aliphatic) primary and secondary amines being examples of such polar organic media. Hydroxy acid (HA) will be the monomer product where water or an acid is the medium; an ester of HA where an alcohol is the medium; or an HA amide where an amine or diamine is the medium. The depolymerization product, if not discarded, can be used as such or used in PHA production.

The amount of medium used affects the time of depolymerization and the percent depolymerization in a given time. Normally a molar ratio of medium to HA moieties of 1:1 to 100:1 will effect optimum depolymerization.

Of course in a landfill lower water to HA ratios frequently will be encountered. Nevertheless, under most landfill conditions of moisture and temperature adequate depolymerization to pulverize film and similar products predominantly of lactic and/or glycolic acid polymer units will occur in a few months, preferably 3-6 months. This is to be contrasted to the 6 months to 2 years normally needed for significant PHA product depolymerization in a landfill.

Since the depolymerization of PHA's by the present invention is a surface reaction, increasing the surface area such as by shredding or pulverizing the PHA expedites depolymerization degradation. As noted previously, the inclusion of a surfactant, conveniently by blending it, along with the quaternary ammonium compound, into the polymer, has been found to further speed the depolymerization. Preferably a non-ionic surfactant, such as a lauryl alcohol/ethylene oxide surfactant, in an amount of 0.1-1%, is used.

If the depolymerization product is to be recovered and reused a very important economical aspect of the present process is the speed of the depolymerization. By selecting optimal reaction conditions, particularly pressure and temperature, significant quantities of PHA can be batch depolymerized often in shredding in as little as 15 minutes. Reactor design, i.e., agitation, shredding, etc., also plays an important role in reaction rate. Where speed is less a factor than other economies, batch times as long as 16 hours may be appropriate.

Continuous process depolymerization can be provided, e.g. by continuously introducing feed materials into the first depolymerization stage of a multistage system, and recovering the monomer and/or oligomer product from the last stage. The medium and the quaternary ammonium compound can be recycled to the first stage.

In selecting any system of PHA/solvent/quat enhancer it is desirable to avoid a system wherein precipitation of the quaternary ammonium enhancer out of the solvent will occur, and this is one reason why quats soluble in the particular solvent selected for the depolymerization medium are preferred over insoluble quats.

In addition to the above-described PHA/quat compositions and stock materials or articles obtained therefrom, other aspects of this invention are encompassed by the foregoing disclosure and include the methods for enhancing the degradability of the PHA and forming the articles or stock materials, the method for depolymerizing the PHA (and recovering HA and/or oligomer products), and the compositions in which degradation of the PHA takes place. Such compositions comprise the depolymerization-enhanced PHA plus a depolymerizing solvent (which is preferably a solvent both for depolymerization products such as HA's and HA oligomers and for the quat) in contact with the quat-containing PHA.

In the depolymerization method of this invention, the quat-containing PHA is contacted with the depolymerization solvent medium which is preferably a solvent for the PHA hydrolysis products and the quaternary ammonium compound.

The following non-limiting examples illustrate the preferred practice of the present invention. In these examples, abbreviated expressions such as "HAA", "LA", etc. are explained in footnotes. Expressions such as "PHA" have been previously defined. All parts and percentages are by weight unless otherwise indicated.

EXAMPLES 1 & 2

5 g samples of PHA are prepared. Some contain no quaternary ammonium salt. Others containing 1% by weight of the quaternary ammonium salt (quat) of octyl trimethylammonium bromide, which is in the form of finely ground powder, intimately mixed into the molten polymer in a stirred flask. The quat is substantially uniformly distributed throughout the polymer. The polymer samples are in the form of ground particles about ⅛ inch in average diameter, with quat present in the particle surfaces and uniformly throughout.

Each 5 g polymer sample is placed into beakers containing 100 cc of water at 92° C., and let stand for 30 days without stirring. The percentage of weight lost over 30 days is used to measure the rate of hydrolysis degradation. Table 1 shows the results of these tests.

TABLE 1

| Example | Polymer | % Weight Lost | |
|---|---|---|---|
| | | No Quat | 1% Quat |
| 1 | 55/45 HAA/LA[1] MW 1200 | 35 | 48 |
| 2 | 90/10 L/DL LA[2] MW 25000 | 12 | 23 |

[1]Copolymer of 55% (by weight) of hydroxyacetic acid (HAA) and 45% of L-lactic acid (LA), average polymer molecular weight of 1200.
[2]Copolymer of 90% of L- and 10% of D/L lactic acid, average molecular weight of 25,000.

In these tests, the presence of the quaternary ammonium salt increased the hydrolysis degradation of both low and high molecular weight PHA polymers by about 35-50%.

EXAMPLES 3, 4 & 5

(Comparison)

The procedure of Examples 1 and 2 is followed excepted as noted. Polymer samples are prepared, except that no samples contain any quaternary ammonium salt. Instead, 2% by weight of the polymer (the same amount as in Examples 1 and 2) of the same quaternary ammonium salt was added to the water in half of the beakers containing the polymer. The tests were continued for 55 days. Table 2 shows the weight losses in these tests.

TABLE 2

| Example | Polymer | % Weight Lost | |
|---|---|---|---|
| | | No Quat | 1% Quat |
| 3 | HAA[3] MW 1800 | 22 | 21 |
| 4 | 55/45 HAA/LA[1] MW 1200 | 45 | 48 |
| 5 | 90/10 L/DL LA[2] MW 25000 | 18 | 20 |

[3]Hydroxyacetic acid homopolymer
[1]See Example 1
[2]See Example 2

In Examples 3-5, where the quat is put into the depolymerization medium (water) instead of in the polymer in accordance with the present invention, the quat has little or no effect on the rate of depolymerization.

EXAMPLES 6-8

The procedure of Examples 1 and 2 is followed except as noted. In addition to the quat in all of the polymer samples, the non-ionic surfactant MERPOL HCS (a fatty alcohol ethylene oxide condensate made by the Du Pont Company) in the amount of 1% of the weight of the polymer is blended intimately into the molten polymer. The test duration is 26 days. Table 3 shows the results of these tests.

TABLE 3

| Example | Polymer | % Weight Lost | |
|---|---|---|---|
| | | No Surfactant | Surfactant |
| 6 | 90/10 L/DL LA[2] MW 25000 | 26 | 30 |
| 7 | 55/45 HAA/LA[1] MW 1200 | 49 | 63 |
| 8 | HAA[3] MW 1000 | 21 | 24 |

[2]See Example 2
[1]See Example 1
[3]See Example 3

The results of these Examples show that the inclusion of surfactant in the polymer along with quat further enhances the depolymerization.

EXAMPLES 9-14

Following the procedure of Examples 1 and 2, the polymer/quat compositions shown in Table 4 are prepared and tested in comparison to the polymer without any quat. The polymer/quat samples exhibit significantly enhanced depolymerization.

TABLE 4

| Example | Polymer | Quat |
|---|---|---|
| 9 | 90/10 L/DL LA[2] MW 100,000 | tetrabutylammoniumbromide (TBAB) |
| 10 | HAA[3] MW 50,000 | methyltributylammonium chloride (MTBC) |
| 11 | 70/10/20 GLY/LA/CL[4] MW 50,000 | octyltrimethyl ammonium chloride (OTMAB) |
| 12 | 100 PH/BA[5] MW 50,000 | tetrabutylammonium bromide (TBAB) |
| 13 | 80LA/20VL[6] MW 25,000 | benzyltrimethylammonium chloride (BTAC) |
| 14 | 95/5 LA[7] MW 50,000 | choline chloride |

[2]See Example 2
[3]See Example 3
[4]70% glycolide, 10% lactide, 20% caprolactone terpolymer
[5]100% polyhydroxybutyricacid
[6]80% L-lactide/20% valerolactone
[7]95% L-lactide, 5% D/L-lactide

EXAMPLES 15 & 16

The procedure of Example 1 and 2 are repeated except that 100 cc of methanol are used in place of 100 cc of water. Enhanced depolymerization of the polymers is noted.

What is claimed is:

1. A hydroxyzable composition comprising poly(hydroxyacid) polymer containing, in an amount adequate to depolymerize said polymer, an ammonium salt or a quaternary ammonium compound substantially, fully distributed there through the polymer, said polymer being selected from the group consisting of polylactide, polyglycolide, copolymers of lactide and glycolide, and polymers containing a major proportion of lactide or glycolide units or combinations thereof, polymerized with up to 30% of at least one of the monomers epsilon-caprolactone, delta-valerolactone, 1,5 dioxepen-2-one, 1,4-dioxan-2-one, beta-butyrolactone, beta-propiolactone, 6-methyl-2,5-morpholinedione.

2. The composition of claim 1 wherein the quaternary ammonium compound is a substantially neutral salt represented by the formula

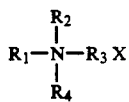

wherein $R^1$, $R^2$, $R^3$ and $R^4$ can be the same or different and are aliphatic, cycloaliphatic, or aromatic radicals, or two or more of the groups $R_1$ through $R_4$ can, together with the N-atom, form a heterocyclic ring, and X is the anion of an organic or mineral acid.

3. The composition of claim 1 wherein $R_1$ to $R_4$ are alkyl, including substituted alkyl, and the quaternary ammonium compound is one or more of the following salts:
tetrabutylammonium bromide,
benzyltrimethylammonium chloride,
methyltricaprylammonium chloride,
methyltributylammonium chloride,
triethylbenzylammonium chloride,
octyltrimethylammonium bromide, or
choline chloride.

4. The composition of claim 1 wherein the weight amount of quaternary ammonium compound is in the range of 0.1 to 10% by weight of poly(hydroxyacid).

5. The composition of claim 1 wherein said polymer consists essentially of polylactic acid.

6. The composition of claim 1 wherein said polymer comprises a major proportion of lactide units.

7. The composition of claim 1 wherein said composition includes a surfactant substantially fully distributed through the poly(hydroxyacid).

8. A molded article comprising the composition of claim 1.

9. A composition for depolymerization comprising a hydroxyzable poly(hydroxyacid) polymer containing substantially fully distributed therethrough 0.1 to 10% by weight of a quaternary ammonium compound that is reactive with said polymer and a solvent for the depolymerization products of said polymer and said quaternary ammonium compound, said solvent being in contact with said polymer containing the quaternary ammonium compound said poly(hydroxyacid) being selected from the group consisting of polylactide, polyglycolide, copolymers of lactide and glycolide, and polymers containing a major proportion of lactide or glycolide units or combinations thereof, polymerized with up to 30% of at least one of the monomers epsilon-caprolactone, delta-valerolactone, 1,5 dioxepen-2-one, 1,4 dioxan-2-one, beta-butyrolactone, betapropiolactone, 6-methyl-2,5-morpholinedione.

10. The composition of claim 9 wherein the molar ratio of solvent to hydroxyacid moieties is in the range 1:1 to 100:1.

11. The composition of claim 9 wherein the solvent is a protic polar organic liquid or ammonia.

12. The composition of claim 9 wherein the weight ratio of quaternary ammonium compound to poly(hydroxyacid) is in the range 0.5 to 10% of the weight of the polymer.

13. A molding composition comprising
a moldable solid hydroxyzable said poly(hydroxyacid) selected from the group consisting of polylactide, polyglycolide, copolymers of lactide and glycolide, and polymers containing a major proportion of lactide or glycolide units or combinations thereof, polymerized with up to 30% of at least one of the monomers epsilon-caprolactone, delta-valerolactone, 1,5 dioxepen-2-one, 1,4 dioxan-2-one, beta-butyrolactone, betapropiolactone, 6-methyl-2,5-morpholinedione, and, substantially fully distributed therethrough,
about 0.1 to about 10% by weight, based on the weight of the poly(hydroxycarboxylic acid), of a quaternary ammonium salt of the formula

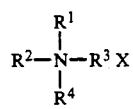

wherein $R^1$, $R^2$, $R^3$, and $R^4$ are alkyl, unsubstituted or substituted by oxy, amido, or aryl, and X is the anion of a mineral acid or organic acid.

14. A molding composition according to claim 13, comprising said poly(hydroxycarboxylic acid), said quaternary ammonium salt, and about 0.1 to about 1% by weight, based on the weight of the poly(hydroxycarboxylic acid), of a nonionic surfactant.

15. A method for recovering a hydroxyacid from a composition of claim 1, said method comprising:
bringing a depolymerization medium into contact with a said composition and depolymerizing the poly(hydroxyacid) in said composition of claim said depolymerization medium providing a medium for interaction of the poly(hydroxyacid) and the quaternary ammonium compound of said composition, and
recovering substantially monomeric hydroxyacid from said medium.

16. A method according to claim 15, wherein the depolymerization medium is a solvent for the substantially monomeric hydroxyacid.

17. A method according to claim 16, wherein the solvent is water, ammonia, an acid, an alcohol, an amine, or a mixture thereof.

18. A method according to claim 16, wherein the molar ratio of solvent to hydroxyacid moieties in the poly(hydroxyacid) is in the range 1:1 to 100:1.

19. A method for preparing a degradable poly(hydroxyacid) molding composition of claim 13, comprising the steps of
adding a finely divided particulate solid quaternary ammonium compound to the poly(hydroxyacid) while said poly(hydroxyacid) is in the form of a molten mass, and
blending the finely divided particulate solid quaternary ammonium compound with the molten mass until the particles of the quaternary ammonium compound are substantially fully distributed throughout the molten mass.

20. A method for preparing a degradable poly(hydroxyacid) molding composition of claim 13, comprising the steps of (a) polymerizing one or more monomers of the formulas I, II, and III

 (I)

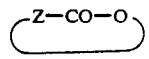 (II)

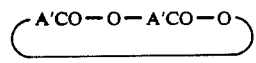 (III)

where

A is a straight or branched aliphatic chain which can contain one or more heteroatoms in place of carbons in the aliphatic chain, and A contains from 1 to 8 carbon atoms in the backbone of the chain;

A' is a straight or branched chain lower alkylene group of the formula $-C(R^1)(R^2)-C(R^3)(R^4)-$, where $R^1$ to $R^4$ are the same or different and are H or methyl; and Z is the aliphatic residue of a lactone, which residue can contain one or more hetero-atoms;

(b) introducing the quaternary ammonium compound into the resulting polymer and substantially fully distributing said compound throughout said polymer before the polymerization reaction is completed.

* * * * *